United States Patent
Fowler, Jr.

[11] Patent Number: 6,117,072
[45] Date of Patent: Sep. 12, 2000

[54] PLASTIC STAY ASSEMBLY FOR USE WITH MRI AND X-RAY IMAGING SYSTEMS

[75] Inventor: James M. Fowler, Jr., Houston, Tex.

[73] Assignee: Lone Star Medical Products, Inc., Houston, Tex.

[21] Appl. No.: 09/221,798

[22] Filed: Dec. 28, 1998

[51] Int. Cl.[7] .................................................. A61B 17/00
[52] U.S. Cl. ..................... 600/217; 600/210; 600/235; 600/231; 600/233
[58] Field of Search ................................. 600/210, 217, 600/227, 231, 232, 233, 235, 201

[56] References Cited

U.S. PATENT DOCUMENTS

| | | |
|---|---|---|
| 170,573 | 11/1875 | Lesh ........................................ 24/300 X |
| 334,711 | 1/1886 | Lorenz ............................ 24/265 EE X |
| 3,515,129 | 6/1970 | Truhan . |
| 3,542,015 | 11/1970 | Steinman ............................ 600/206 X |
| 3,655,964 | 4/1972 | Slight ................................... 250/43.5 D |
| 3,749,088 | 7/1973 | Kohlmann . |
| 3,762,401 | 10/1973 | Tupper . |
| 3,916,879 | 11/1975 | Cotten . |
| 4,048,987 | 9/1977 | Hurson .................................... 600/206 |
| 4,185,636 | 1/1980 | Gabbay et al. . |
| 4,190,042 | 2/1980 | Sinnreich . |
| 4,254,763 | 3/1981 | McCready et al. . |
| 4,257,406 | 3/1981 | Schenk . |
| 4,263,900 | 4/1981 | Nicholson . |
| 4,274,398 | 6/1981 | Scott, Jr. . |
| 4,321,916 | 3/1982 | McKee . |
| 4,337,762 | 7/1982 | Gauthier . |
| 4,337,763 | 7/1982 | Petrassevich . |
| 4,344,420 | 8/1982 | Forder . |
| 4,355,631 | 10/1982 | LeVahn . |
| 4,380,999 | 4/1983 | Healy . |
| 4,387,706 | 6/1983 | Glass . |
| 4,412,532 | 11/1983 | Anthony . |
| 4,421,107 | 12/1983 | Estes et al. . |
| 4,421,108 | 12/1983 | Cabrera et al. . |
| 4,430,991 | 2/1984 | Darnell . |
| 4,434,791 | 3/1984 | Darnell . |
| 4,559,677 | 12/1985 | Tracy ........................................ 24/300 |
| 4,685,467 | 8/1987 | Cartmell et al. ...................... 128/640 |
| 5,080,088 | 1/1992 | LeVahn .................................. 600/206 |
| 5,141,973 | 8/1992 | Kobayaski et al.d .................. 523/300 |
| 5,231,974 | 8/1993 | Giglio et al. ........................... 600/206 |
| 5,260,576 | 11/1993 | Sommer, Jr. et al. ............... 250/359.1 |
| 5,307,805 | 5/1994 | Byrne ................................. 600/227 X |
| 5,512,038 | 4/1996 | O'Neal et al. ..................... 600/235 X |
| 5,518,124 | 5/1996 | Sommer, Jr. et al. .................. 209/577 |
| 5,738,224 | 4/1998 | Sommer, Jr. et al. .................. 209/588 |
| 5,769,783 | 6/1998 | Fowler, Jr. ............................. 600/226 |
| 5,785,649 | 7/1998 | Fowler, Jr. ............................. 600/233 |
| 5,899,853 | 5/1999 | Fowler, Jr. ............................. 600/217 |
| 5,964,697 | 10/1999 | Fowler, Jr. ............................. 600/210 |
| 5,964,698 | 10/1999 | Fowler .................................. 600/217 |

FOREIGN PATENT DOCUMENTS

| | | |
|---|---|---|
| 1222141 | 2/1971 | United Kingdom . |
| 1550254 | 8/1979 | United Kingdom . |
| 1550255 | 8/1979 | United Kingdom . |

OTHER PUBLICATIONS

Bone Retractors and Retractors AESCULAP©, Product catalog p. 319 (no date).

Thermoplastic Replaces Metal in Disposable Abdominal Retractor, MD&M Review, ULTOP® Conveyor Modules (no date).

I.S.I. North America, Inc. *International Surgical Instruments* Brochure (1990).

*Accurate Surgical & Scientific Instruments Corporation* Brochure (no date).

*Primary Examiner*—Jeffrey A. Smith
*Attorney, Agent, or Firm*—Akin, Gump, Strauss, Hauer & Feld, LLP

[57] ABSTRACT

An improved surgical retractor stay having a plastic hook member such that the entire surgical retractor stay is substantially non-interfering with X-ray and MRI imaging techniques.

48 Claims, 2 Drawing Sheets

PLASTIC STAY ASSEMBLY FOR USE WITH MRI AND X-RAY IMAGING SYSTEMS

SPECIFICATION

BACKGROUND OF THE INVENTION

1. Field of the Invention

The present invention relates to surgical retractors and surgical retractor stays. More particularly, the present invention relates to a plastic retractor stay assembly for use in surgical retractor stays wherein the hook member of the retractor stay is formed from a material which is substantially non-interfering with magnetic fields or X-rays used in such medical diagnostic methods such as MRI (magnetic resonance imaging), CAT (computer aided tomography) scans and standard X-ray techniques.

2. Description of the Related Art

During the course of a surgical procedure or operation, the surgeon opens the patient with a scalpel, forming an incision and surgical site. As the surgeon cuts deeper, the operating room staff typically holds tissue away from the operative field using one or more retractors.

Most retractors are one piece metallic implements or have a metallic hook member for securing tissue and holding the tissue away from the operating field as in U.S. Pat. No. 5,785,649 which is incorporated by reference. One common medical diagnostic imaging technique is MRI imaging. MRI imaging requires the application of a high field homogeneous magnetic field to the surgical area of the patient. Other common diagnostic techniques are CAT scans and standard X-ray imaging which require application of X-ray radiation to the surgical area of the patient.

BRIEF SUMMARY OF THE INVENTION

The present invention provides an improved surgical retractor stay and retractor stay assembly that offers several benefits over the prior art.

According to the invention a surgeon can now employ a substantially non-interfering surgical retractor stay, a retractor stay apparatus, and a retractor stay system which may remain in place holding an incision open while a medical diagnostic technique such as MRI or CAT scan is conducted.

The metallic hook members of the retractor stays and the surgical stay apparatus introduce inhomogeneinities into the applied magnetic field used in MRI imaging thereby creating signal loss, signal void, image distortion, image artifacts and image disruption. Metal hooks when used in a surgical stay apparatus also cause substantial signal loss, signal void, image distortion, image artifacts and image disruption both in standard X-ray surgical procedures and CAT scans by blocking or scattering the X-rays. It is sometimes desirable to perform a medical diagnostic imaging analysis of the patient prior to removing the retractor stay and closing the incision. This necessitates performing the medical diagnostic imaging analysis in the presence of the metallic hook members of the surgical stays. The non-interfering hooks according to the invention allow these various diagnostic procedures to be performed unimpeded.

One embodiment of the present invention provides a plastic hook member that is formed from a plastic that is substantially non-inferring with medical diagnostic techniques using magnetic fields and radio frequency electromagnetic radiation such as an MRI.

One embodiment of the present invention also provides a plastic hook member that is substantially non-interfering with medical diagnostic techniques requiring the use of X-ray radiation such as computer aided tomography (CAT).

BRIEF DESCRIPTION OF THE DRAWINGS

For a further understanding of the nature, objects, and advantages of the present invention, reference should be had to the following detailed description, read in conjunction with the following drawings, wherein like reference will denote like elements and wherein.

DETAILED DESCRIPTION OF INVENTION

According to the invention a retractor stay, retractor stay apparatus and retractor stay system are made of materials that are substantially non-interfering with MRI and X-ray diagnostic imaging techniques. According to the invention the retractor stay and retractor stay apparatus permit the surgeon to retract the tissue around an incision and then obtain an MRI or X-ray image with little or no image error.

Figure 1:
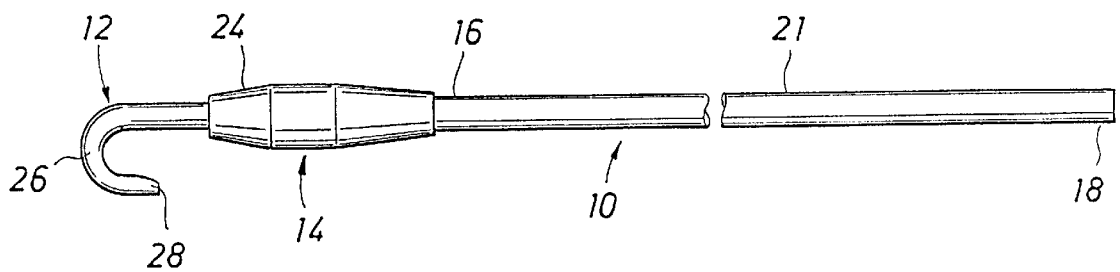
FIG. 1 is a side, elevational view of an embodiment of the apparatus of the present invention.
Figure 2:
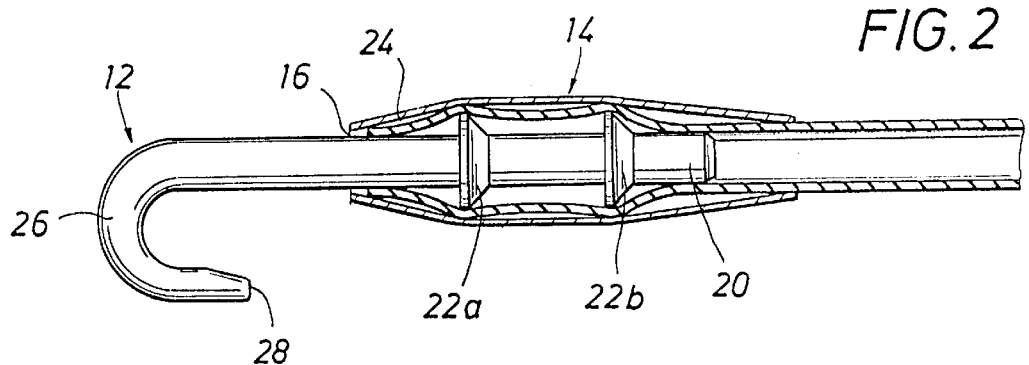
FIG. 2 is a sectional view of the restriction band and handle.
Figure 8:
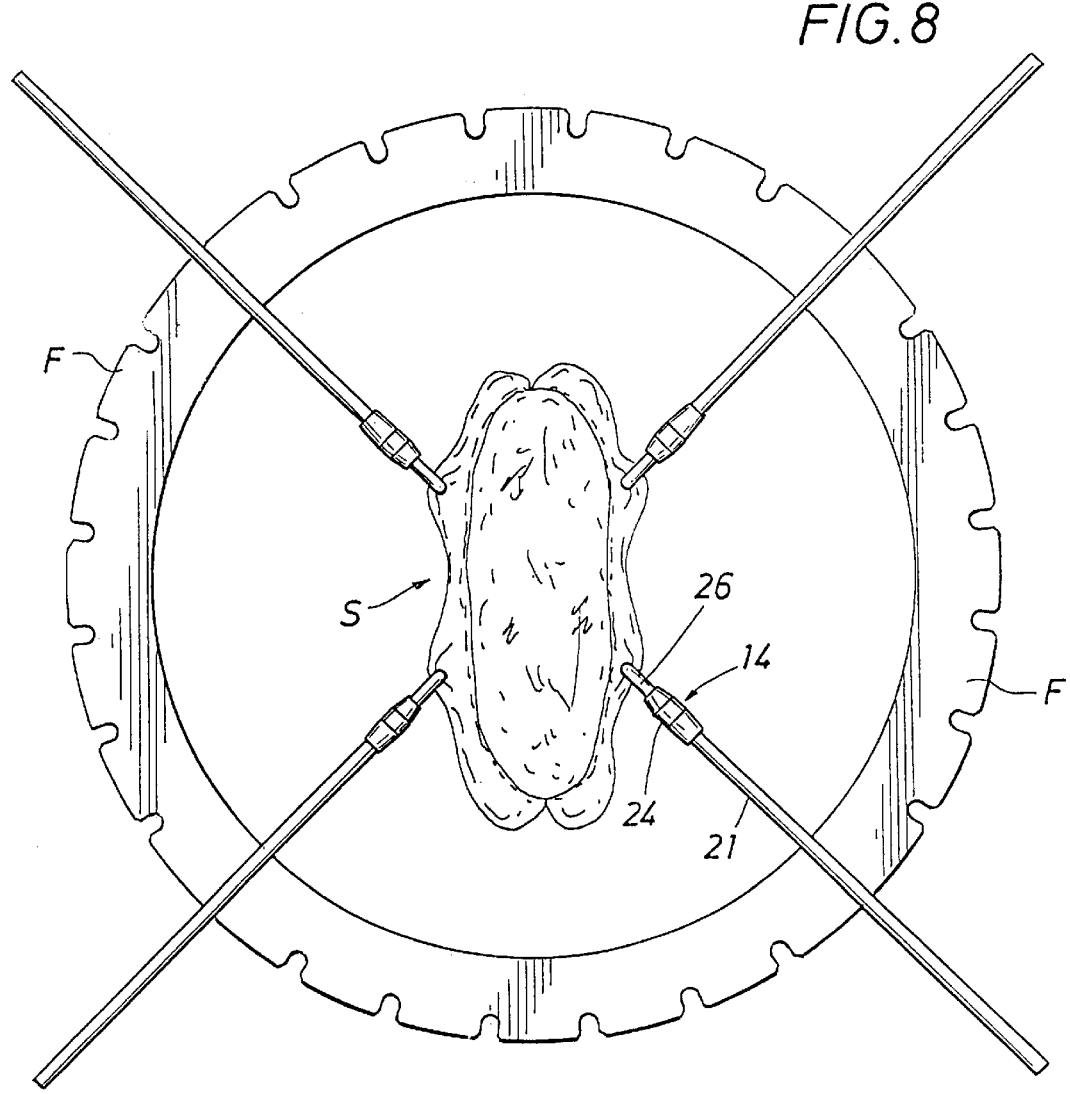
FIG. 8 is a plan view of an embodiment of the retractor stay apparatus in a frame around an incision.
Figure 6:
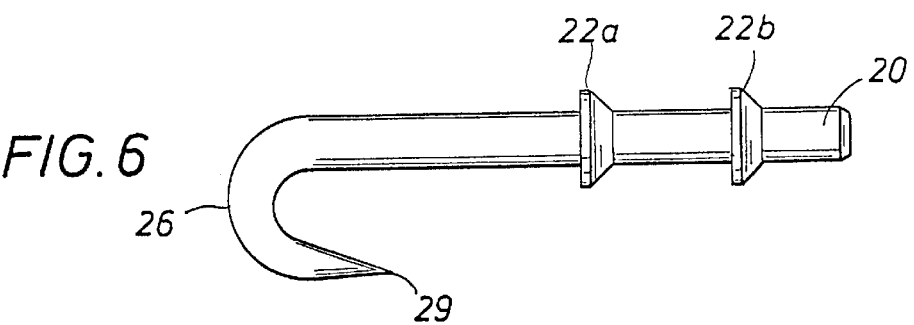
FIG. 6 is a side, elevational view of an embodiment of the hook member having a sharp point.
Figure 7:
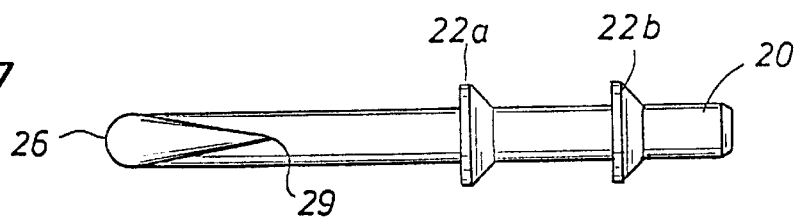
FIG. 7 is a bottom view of an embodiment of the hook member having a sharp point.

FIGS. 1–2 show an embodiment of the surgical retractor stay and surgical retractor stay apparatus according to the present invention designated generally by the numeral 10. As shown in FIG. 2, the surgical stay apparatus 10 includes a hook member 12 that is partially embedded or encapsulated within an elastic member 21 forming a handle 14. The surgical retractor stay apparatus has a proximal end 16 and a distal end 18. The handle 14 may be formed by injection molding or alternatively may be formed by insertion of the proximal straight end portion 20 of the hook member 12 into the proximal end portion 16 of the elastic member 21. The elastic member 21 generally has a uniform diameter although an elastic member 21 having a non-uniform diameter may be used. In FIG. 8, surgical stay apparatus 10 is shown in use during a surgical procedure and attached to frame F that surrounds a surgical site S. The use of frame F and its slots for receiving a surgical retractor stay can be seen and is described in prior U.S. Pat. Nos. 5,785,649 and 4,430,991, incorporated herein by reference.

Hook member 12 is embedded or molded within the handle 14 as shown on FIGS. 1 and 2. The proximal straight end portion 20 of the hook member 12 includes a pair of enlarged diameter sections 22A and 22B. The proximal end portion 20 of the hook member 12 encapsulated in the handle 14 is much longer than the exposed distal end portion 26 of the hook member 12. A majority of the length of the hook member 12 is embedded within the handle 14, which closely conforms to the hook member 12, to develop the connection between the enlarged diameter sections 22A and 22B of hook member 12 with the handle 14. This reduces the possibility that the hook member 12 will pull out of the handle 14 while under tension during use.

The handle 14 is further encased in a heat shrink material which forms a restriction band 24. The restriction band 24 surrounds the handle 14 and extends from the proximal end 16 of the surgical stay assembly to slightly beyond the proximal straight end portion 20 of the hook member 12 in the elastic member 21. The restriction band 24 restricts radial expansion of the elastic member of handle 14. The restriction band 24 promotes additional frictional force between the elastomeric material of the handle 14 and the proximal straight end portion 20 of the hook member 12. This reduces accidental dislocation of the hook member from the handle 14 during a surgical procedure.

Figure 3:
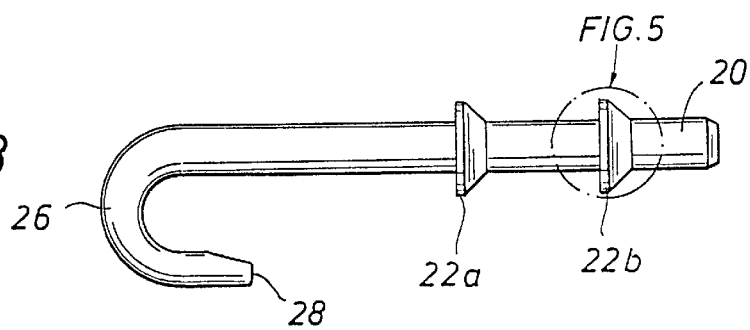
FIG. 3 is a side, elevational view of an embodiment of the hook member having a rounded point.
Figure 4:
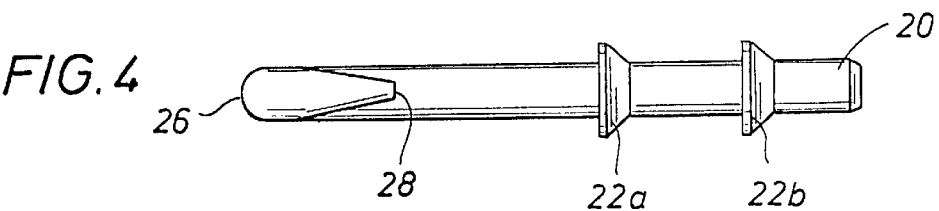
FIG. 4 is a bottom view of an embodiment of the hook member having a rounded point.
Figure 5:
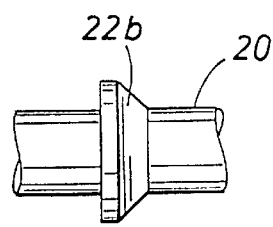
FIG. 5 is a side, elevational enlargement of the increased diameter section of the hook member.

The details of the construction of the hook member 12 are shown in FIGS. 3–7. The hook member 12 includes a proximal straight end portion 20 that communicates with a distal curved or hooked portion 26. The distal curved portion 26 has a point for engaging and holding tissue during use. The point may be either tapered having a sharp point 29 or a rounded point 28 having a radius of curvature ranging from about 0.00" (being a sharp point) to about 0.02". The rounded point of one embodiment according to the present invention has a radius of curvature which typically ranges from about 0.01" to about 0.02". However, the desired radius of curvature of the rounded point 28 varies depending upon the particular surgical application. The value of the radius of curvature of a round point 28 may be chosen so as to provide an effective hook for maintaining the tissue in a retracted position, without slippage, during a surgical procedure. Distal curved portion 26 is generally semicircular, extending through an angle of from about 90° to about 180° as shown in FIG. 3.

One embodiment of the hook member has two enlarged diameter sections located on the proximal straight end portion 20 as shown in FIGS. 3, 4, 6 and 7. The enlarged diameter sections 22A and 22B are generally cone shaped and extend from the proximal straight end portion 20 at an acute angle relative to the proximal straight end portion 20. At their maximum diameters, the enlarged diameter sections 22A and 22B then become parallel to the proximal straight end portion 20 of the hook member 12 for a short distance and then return at a right angle back to the proximal straight end portion 20. In one embodiment the acute angle is about 48° and a preferred maximum diameter of the enlarged diameter section is approximately 175% of the diameter of the proximal straight end portion 20.

According to the invention, the hook member 12 is made from a material that is substantially non-interfering with MRI. For example, one such material is a non-metallic, synthetic plastic or polymer. The synthetic plastic can be selected from the group consisting of, for example, polyphenylene oxide (sold by General Electric under the trademark NORYL), polycarbonate (sold by General Electric under the trademark LEXAN) and nylon 6.

All plastics may not have sufficient tensile strength to avoid deformation of the hook member 12 when the hook member 12 is subjected to stress while holding the tissue in a retracted position. Further, the minimum tensile strength can become increasingly important as the size of the hook member 12 decreases. Decreased size of the hook member 12 is typically desirable because it reduces visual obstruction of the surgeon as well as reduces interference with medical diagnostic imaging procedures. In order to reduce deformation or creep of the plastic hook member 12 during a surgical procedure, the plastic preferably has a tensile strength of about 10,000 psi.

Lower density plastics or polymers typically create less interference with X-rays than the same thickness of a higher density polymer. This may allow a lower density hook member with larger dimensions than a higher density hook member to be used to gain additional strength without degrading the X-ray signal. For hook members with comparable dimensions, but different chemical composition, the hook member made of a plastic having the higher atomic number elements interferes more with X-rays. Plastics with lower atomic number elements may be thicker and therefore stronger, without degrading the X-ray signal, than those with higher atomic number elements. In order for the plastic hook member to have a minimal effect on electromagnetic radiation the plastic may have a density of from about 1.0 grams/cc to about 1.35 grams/cc. The plastic may be non-crystalline.

The absorption coefficient of X-rays is related to the fourth power of the atomic number of an element. As a result, plastics made from elements with low atomic numbers are X-ray transparent at lower X-ray intensities than plastics made with high atomic number elements. Preferred plastics are those which consists essentially of chemical elements having atomic numbers selected from the group consisting of 1, 6, 7, 8, 9 and 14.

According to the present invention the improved surgical stay apparatus are made of materials that are substantially non-interfering with MRI and X-ray imaging diagnostic techniques. According to the present invention the surgical stay and surgical stay apparatus may be employed to retract the tissue of a surgical incision while an MRI or X-ray image is obtained without imaging error caused by the surgical stay or surgical stay apparatus.

The foregoing disclosure and description of the invention are illustrative and explanatory thereof, and various changes in the details of the illustrated apparatus and construction and method of operation may be made without departing from the spirit of the invention.

What is claimed is:

1. A surgical retractor stay for use with X-ray or MRI imaging comprising:
   a) a handle having a proximal end and a distal end and
   b) a plastic hook member having proximal and distal end portions, the proximal end portion being encapsulated by the distal end of the handle, and wherein the plastic consists essentially of chemical elements having atomic numbers selected from the group consisting of 1, 6, 7, 8, 9 and 14 and further wherein the handle and the hook member are both substantially non-interfering with the X-ray or MRI imaging.

2. The surgical retractor stay of claim 1 wherein the handle closely conforms to a majority of the hook member.

3. The surgical retractor stay of claim 1 wherein the proximal end portion of the hook member is inserted into an elastic member to form the handle.

4. The surgical retractor stay of claim 3 wherein the elastic member is of generally uniform diameter.

5. The surgical retractor stay of claim 1 wherein the plastic hook member has an exposed distal end portion that extends through a bend of about 90° to about 180°.

6. The surgical retractor stay of claim 1 wherein the proximal end portion of the plastic hook member encapsulated in the handle is much longer than the unencapsulated distal end portion of the hook member.

7. The surgical retractor stay of claim 1 wherein the hook member further comprises a tapered point.

8. The surgical retractor stay of claim 1 wherein the hook member further comprises a rounded point.

9. The surgical retractor stay of claim 8 wherein the rounded point has a radius of curvature of from about 0.01" to about 0.02".

10. The surgical retractor stay of claim 1 wherein the plastic has a density of from about 1.0 grams/cc to about 1.35 grams/cc.

11. The surgical retractor stay of claim 1 wherein the plastic is non-crystalline.

12. A surgical retractor stay for use with X-ray or MRI imaging comprising:
(a) a handle having a proximal end and a distal end and
(b) a plastic hook member having proximal and distal end portions, the proximal end portion being encapsulated by the distal end of the handle wherein the handle and the hook member are both substantially non-interfering with the X-ray or MRI imaging and wherein the plastic is selected from the group consisting of polyphenylene oxide, polycarbonate and nylon 6.

13. A surgical retractor stay for use with X-ray or MRI imaging comprising:
(a) a handle having a proximal end and a distal end and
(b) a plastic hook member having proximal and distal end portions, the proximal end portion being encapsulated by the distal end of the handle wherein the handle and the hook member are both substantially non-interfering with the X-ray or MRI imaging and further wherein the plastic has a tensile strength of about 10,000 psi.

14. A surgical retractor stay apparatus comprising:
a) a handle body having proximal and distal ends;
b) a plastic hook member having proximal end portion and a distal portion, the proximal end portion of the plastic hook member encapsulated by the distal end of the handle, the distal end of the handle closely conforming to the encapsulated portion of the hook member;
c) an elastic member integrally connected to the proximal end of the handle, the elastic member having an elongated portion that extends from the distal end of the handle; and
d) the hook member having an exposed curved portion extending from the distal end portion of the handle; and
e) a restrictive band encircling the handle;
f) wherein the surgical stay apparatus is substantially non-interfering with medical diagnostic techniques comprising using magnetic fields or X-rays.

15. The surgical retractor stay apparatus of claim 14 wherein the handle closely conforms to a majority of the hook member.

16. The surgical retractor stay apparatus of claim 14 wherein the proximal end of the hook member is inserted into the elastic member to form the handle.

17. The surgical retractor stay apparatus of claim 14 wherein the elastic member is of generally uniform diameter.

18. The surgical retractor stay apparatus of claim 14 wherein the plastic hook member has an exposed distal end portion that extends through a bend of about 90° to about 180°.

19. The surgical retractor stay apparatus of claim 14 wherein the proximal end portion of the plastic hook member encapsulated in the distal end of the handle is much longer than the unencapsulated distal portion of the hook member.

20. The surgical retractor stay apparatus of claim 14 wherein the hook member further comprises a tapered point.

21. The surgical retractor stay apparatus of claim 14 wherein the hook member further comprises a rounded point.

22. The surgical retractor stay apparatus of claim 21 wherein the rounded point has a radius of curvature of from about 0.01" to about 0.02".

23. The surgical retractor stay apparatus of claim 14 wherein the plastic is selected from the group consisting of polyphenylene oxide, polycarbonate and nylon 6.

24. The surgical retractor stay apparatus of claim 14 wherein the plastic has a tensile strength of about 10,000 psi.

25. The surgical retractor stay apparatus of claim 14 wherein the plastic has a density of from about 1.0 grams/cc to about 1.35 grams/cc.

26. The surgical retractor stay apparatus of claim 14 wherein the plastic is non-crystalline.

27. The surgical retractor stay apparatus of claim 14 wherein the plastic consists essentially of elements having atomic numbers selected from the group consisting of 1, 6, 7, 8, 9 and 14.

28. A surgical retractor stay system comprising:
a) a frame that conforms to a patient's body at a surgical site;
b) a stay that includes a handle having proximal and distal ends;
c) a plastic hook member having proximal and distal end portions, the proximal end portion being encapsulated by the handle;
d) an elastic member integrally connected to the distal end of the handle, the elastic member having an elongated portion that extends from the distal end of the handle body, the elastic member and the handle body forming a stay;
e) the hook member having an exposed curved distal portion extending from the distal portion of the handle; and
f) wherein the plastic is non-crystalline and further wherein the surgical retractor stay system is substantially non-interfering with medical diagnostic techniques comprising using magnetic fields or X-rays.

29. The surgical retractor stay system of claim 28 wherein the handle closely conforms to a majority of the hook member.

30. The surgical retractor stay system of claim 28 wherein the proximal end of the hook member is inserted into the proximal end of the handle.

31. The surgical retractor stay system of claim 28 wherein the proximal end of the hook member is inserted into the elastic member to form the handle.

32. The surgical retractor stay system of claim 28 wherein the elastic member is of generally uniform diameter.

33. The surgical retractor stay system of claim 28 wherein the plastic hook member has an exposed portion that extends through a bend of about 90° to about 180°.

34. The surgical retractor stay system of claim 28 wherein the proximal end portion of the plastic hook member encapsulated in the distal end of the handle is much longer than the unencapsulated distal portion of the hook member.

35. The surgical retractor stay system of claim 28 wherein the hook member further comprises a tapered point.

36. The surgical retractor stay system of claim 28 wherein the hook member further comprises a rounded point.

37. The surgical retractor stay system of claim 36 wherein the rounded point has a radius of curvature of from about 0.01" to about 0.02".

38. The surgical retractor stay system of claim 28 wherein the plastic is selected from the group consisting of polyphenylene oxide, polycarbonate and nylon 6.

39. The surgical retractor stay system of claim 28 wherein the plastic body has a tensile strength of about 10,000 psi.

40. The surgical retractor stay system of claim 28 wherein the plastic consists essentially of elements having atomic numbers selected from the group consisting of 1, 6, 7, 8, 9 and 14.

41. A surgical retractor stay system comprising:
   a) a frame that conforms to a patient's body at a surgical site;
   b) a stay that includes a handle having proximal and distal ends;
   c) a plastic hook member having proximal and distal end portions, the proximal end portion being encapsulated by the handle:
   d) an elastic member integrally connected to the distal end of the handle, the elastic member having an elongated portion that extends from the distal end of the handle body, the elastic member and the handle body forming a stay;
   e) the hook member having an exposed curved distal portion extending from the distal portion of the handle; and
   f) wherein the surgical stay system is substantially non-interfering with medical diagnostic techniques comprising using magnetic fields or X-rays and further wherein the plastic body has a density of from about 1.0 grams/cc to about 1.35 grams/cc.

42. A surgical retractor stay system comprising:
   a) a frame that conforms to a patient's body at a surgical site;
   b) a stay that includes a handle having proximal and distal ends;
   c) a plastic hook member having proximal and distal end portions, the proximal end portion being encircled by the handle;
   d) an elastic member integrally connected to the distal end of the handle, the elastic member having an elongated portion that extends from the distal end of the handle body, the elastic member and the handle body forming a stay;
   e) the hook member having an exposed curved distal portion extending from the distal portion of the handle;
   f) a restrictive band encircling the handle; and
   g) wherein the surgical stay system is substantially non-interfering with medical diagnostic techniques comprising using magnetic fields or X-rays.

43. The surgical retractor stay system of claim 42 wherein the elastic member is of generally uniform diameter.

44. The surgical retractor stay system of claim 42 wherein the plastic is selected from the group consisting of polyphenylene oxide, polycarbonate and nylon 6.

45. The surgical retractor stay system of claim 42 wherein the plastic has a tensile strength of about 10,000 psi.

46. The surgical retractor stay system of claim 42 wherein the plastic has a density of from about 1.0 grams/cc to about 1.35 grams/cc.

47. The surgical retractor stay system of claim 42 wherein the plastic is non-crystalline.

48. The surgical retractor stay system of claim 42 wherein the plastic consists essentially of elements having atomic numbers selected from the group consisting of 1, 6, 7, 8, 9 and 14.

* * * * *